United States Patent [19]

Willis et al.

[11] 4,326,997

[45] Apr. 27, 1982

[54] FRAGRANCE COMPOSITIONS OF ALICYCLIC KETONE AND ALCOHOL DERIVATIVES

[75] Inventors: Brian J. Willis, Bergenfield, N.J.; Robert G. Eilerman, Merrick, N.Y.; John M. Yurecko, Jr., Bayonne, N.J.

[73] Assignee: Fritzsche Dodge & Olcott Inc., New York, N.Y.

[21] Appl. No.: 194,967

[22] Filed: Oct. 8, 1980

[51] Int. Cl.[3] .......... A61K 7/46

[52] U.S. Cl. .......... 252/522 R; 568/362; 568/376; 568/377; 568/825; 568/834; 131/276; 426/534

[58] Field of Search .......... 252/522 R; 568/362, 568/376, 377, 825, 830, 834

[56] References Cited

U.S. PATENT DOCUMENTS

| | | | |
|---|---|---|---|
| 4,076,854 | 2/1978 | Light et al. | 252/522 R |
| 4,203,925 | 5/1980 | Barton et al. | 252/522 R |
| 4,246,292 | 1/1981 | Konst et al. | 252/522 R |

OTHER PUBLICATIONS

Arctander, "Perfume and Flavor Chemicals", vols. I & II, Monographs 166, 1749, 2061, 3001, (1969).

*Primary Examiner*—John F. Niebling
*Attorney, Agent, or Firm*—Cooper, Dunham, Clark, Griffin & Moran

[57] ABSTRACT

Alicyclic ketone and alcohol derivatives having the structure:

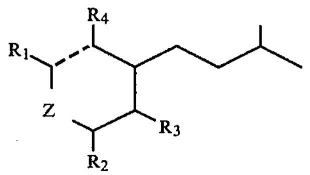

wherein the dotted line represents a carbon-carbon double bond or a carbon-carbon single bond; wherein Z is

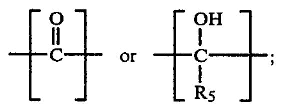

and wherein each of $R_1$, $R_2$, $R_3$, $R_4$, and $R_5$ is hydrogen or lower alkyl are useful as odor-modifying ingredients in perfumes and perfumed products and as flavor-modifying ingredients in foodstuffs and tobacco products. These derivatives may be prepared from substituted phenols having the structure:

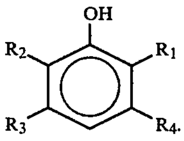

14 Claims, No Drawings

FRAGRANCE COMPOSITIONS OF ALICYCLIC KETONE AND ALCOHOL DERIVATIVES

BACKGROUND OF THE INVENTION

There is considerable demand for materials which are useful in modifying, enhancing, or improving the organoleptic properties of consumable products. The natural oils which traditionally have been used for this purpose suffer the disadvantages of limited supply, high cost, and variable quality. Accordingly, the search for synthetic compounds which can function as partial or total replacements for essential oils or which can be used to create new flavor and fragrance materials has intensified.

Various substituted cyclohexane derivatives having useful organoleptic properties are known. For example, Arctander, *Perfume and Flavor Chemicals,* Vols. 1 and 2, (1969) Montclair, N.J. (U.S.A.) describes the following compounds and their use in perfume and flavor compositions:

(1) "166: para-tertiary-AMYLCYCLOHEXANONE

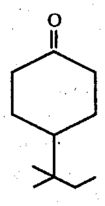

Very powerful, diffusive, woody-camphoraceous odor, slightly earthy, yet with some resemblance to Orris root, overall very dry."

(2) "1749: 1-HYDROXY 2-METHYL-4-tertiary-AMYLCYCLOHEXANE

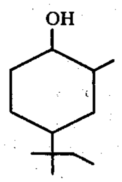

Woody-rootlike, dry-sweet and very tenacious odor with resemblance to Vetiver, Cedar and Amyris."

(3) "2061: METHYl-2-iso-HEXYL-4-CYCLOHEXANONE-1

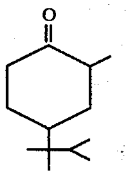

Warm, mild, but tenacious musky-orrislike odor. The camphoraceous notes so often encountered in cyclohexanone derivatives, are pleasantly subdued and generally accepted as Orris-like rather than Camphor-like."

(4) "3001: 1,1,3-TRIMETHYL-2-CYCLOHEXANONE-4 2,4,4-Trimethyl-2-cyclohexen-1-one

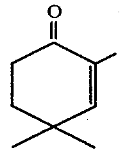

Powerful and rather pungent, but in dilution pleasant, warm-herbaceous and minty-camphoraceous odor, reminiscent of Tansy oil or Dalmation Sage oil."

In addition, Chemical Abstracts, 89, 197052 k (Japanese Pat. No. 78 895,942) discloses preparation of the compound having the structure:

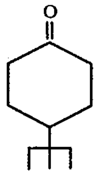

Finally, Chemical Abstracts, 68, 39828 e (L. M. Shulov, et al., Zh. Org. Khim., 3,1819 (1967) discloses preparation of the bicyclic derivative having the structure:

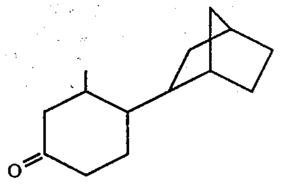

This compound is described as having the fragrance of fresh greens.

Although the preceding compounds are known, no description of the compounds of this invention and no prediction of the compounds or of their advantageous organoleptic properties is known in the prior art.

SUMMARY OF THE INVENTION

Novel compounds, having the structure:

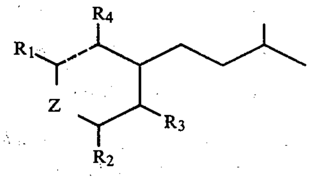

wherein the dotted line represents either a carbon-carbon double bond or a carbon-carbon single bond; wherein Z is either

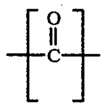
or
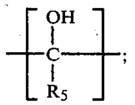

and wherein each of $R_1$, $R_2$, $R_3$, $R_4$, and $R_5$ is hydrogen or lower alkyl, are useful as odor-modifying ingredients in perfumes and perfumed products and as flavor-modifying ingredients in foodstuffs and tobacco products.

The compounds may be prepared by treating substituted phenols having the structure:

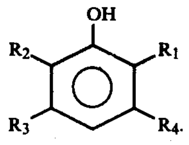

with isoprene or 3-methyl-3-buten-2-ol to form prenylated phenols having the structure:

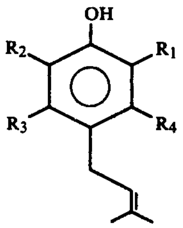

; and converting the prenylated phenols to the compounds of this invention.

DETAILED DESCRIPTION OF THE INVENTION

New flavors, flavoring compositions, perfumes, perfumed articles, and tobacco products can be produced by including therein effective amounts of one or more novel alicyclic ketone or alcohol derivative having the structural formula:

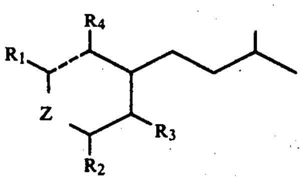

I wherein the dotted line represents a carbon-carbon double bond or a carbon-carbon single bond; wherein Z is either

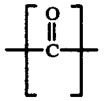

or

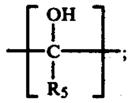

;

and wherein each of $R_1$, $R_2$, $R_3$, $R_4$, and $R_5$ is hydrogen or lower alkyl, that is, $C_1$ to $C_4$ alkyl, particularly, methyl or ethyl. The compounds of this invention can exist in several stereoisomeric forms. Therefore, the structural formulae used herein are intended to embrace the individual stereoisomers as well as mixtures thereof.

In accordance with one embodiment of the invention, compounds I may be produced from substituted phenols having the structure:

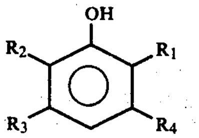

II wherein each of $R_1$, $R_2$, $R_3$, and $R_4$ are as defined for compounds I. Treatment of phenols II with either isoprene or 3-methyl-3-buten-2-ol in the presence of a mineral acid according to known methodology (see, for example, J. Amer. Chem. Soc., 80, 3073 (1958) and Chemical Abstracts, 50, 1654 (1956) results in formation of prenylated phenols having the structure:

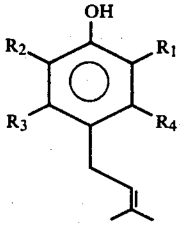

III

Phenols III may also be prepared by a modification of the method of Dewhirst and Rust (J. Org. Chem., 28, 798 (1963)) which involves reacting isoprene with phenols II in the presence of a catalytic quantity of the corresponding aluminum phenoxide.

Conversion of prenylated phenols III to compounds I may be accomplished by the routes outlined in Schemes A and B. Thus, as shown in Scheme A, compounds I may be prepared by hydrogenation of III in the presence of a metal catalyst such as palladium on carbon, or Raney nickel. In this reaction, solvents such as lower alcohols, acetic acid, or mixtures thereof can be employed at temperatures ranging from about 25° to about 300° C., and at variable pressures, the exact conditions depending upon the product desired. For example, hydrogenation of 2,6-dimethyl-4-(3-methyl-2-butenyl)-phenol in the presence of palladium on carbon at temperatures in the range from about 150° to 200° C. and at pressures from about 200 to 300 psig results in formation of cyclohexanone V (wherein $R_1 = R_2 = CH_3$; $R_3 = R_4 = H$) which is useful in perfume and flavor compositions.

Alternatively, 2,6-dimethyl-4-(3-methyl-2-butenyl)-phenol may be reduced to alcohol IV (wherein $R_1 = R_2 = CH_3$; $R_3 = R_4 = H$) in acetic acid with platinum oxide at temperatures from about 50° to 100° C. and pressures from about 200 to 300 psig. The resulting alcohol also possesses interesting organoleptic properties.

SCHEME A

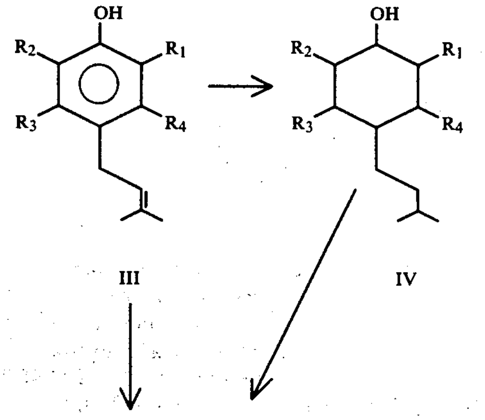

III IV

-continued

SCHEME A

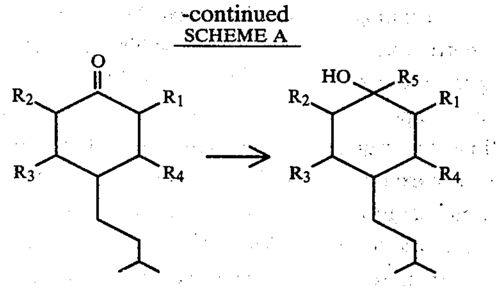

V VI

SCHEME B

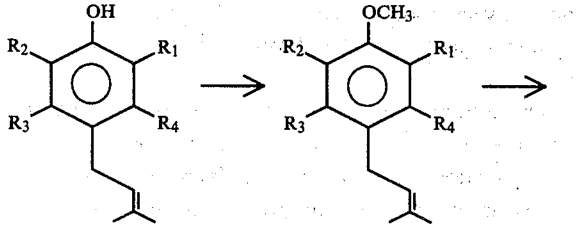

III VII

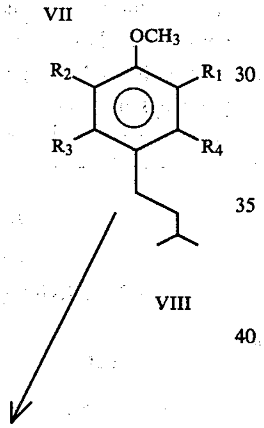

VIII

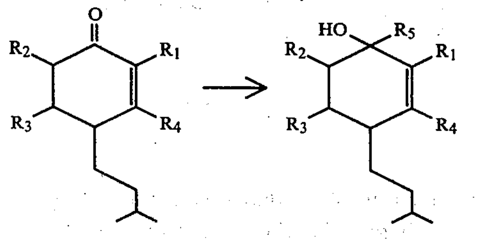

IX X

In addition, alcohol IV may be oxidized with a suitable oxidizing agent such as "Jones" reagent, pyridinium chlorochromate, or sodium dichloromate-sulfuric acid according to known methods to form the corresponding ketone V. (See H. O. House, *Modern Synthetic Reactions,* 2nd ed., W. A. Benjamin, Inc., p. 257, (1972)).

Ketone V may be converted to alcohol VI by reacting the ketone with an organometallic derivative such as a Grignard reagent (e.g. $R_5MgX$) or an organolithium compound (e.g. $R_5Li$) wherein $R_5$ is lower alkyl, that is, $C_1$ to $C_4$ alkyl. This reaction is desirably carried out with a stoichiometric quantity of the organolithium reagent or with excess (2 or 3 equivalents) Grignard reagent. The reaction is preferably carried out in a suitable solvent such as diethyl ether or tetrahydrofuran under an inert atmosphere such as nitrogen or argon, and at temperatures in the range from about −10° to 50° C. Hydrolysis of the resulting organometallic adduct is accomplished with ice-cold dilute mineral acid, or preferably, with saturated ammonium chloride solution, and results in formation of alcohol VI. After recovery and purification, alcohol VI may be utilized in perfume or flavor compositions.

In a further embodiment of the invention outlined in Scheme B, the phenolic hydroxyl group in compound III may be converted by etherification to methyl ether VII. This transformation may be effected by known techniques. (See J. March, *Advanced Organic Chemistry,* 2nd ed., McGraw-Hill Book Company, p. 357, (1977)). For example, the phenol may be treated with an alkali metal hydroxide such as aqueous sodium hydroxide, followed by alkylation with dimethyl sulfate at a temperature from about 25° to 80° C.

If desired, reduction of the olefinic bond in ether VII may be carried out with hydrogen gas in the presence of a hydrogenation catalyst such as 5% palladium on carbon or Raney nickel. This reaction, which is preferably carried out in a Parr reaction vessel at a pressure from about 20 to 80 psig results in production of saturated aromatic ether VIII. Ether VIII may then be converted to enone IX by subjecting the ether to dissolving metal reduction involving treatment with an alkali metal, such as lithium or sodium, in a mixture solvent system containing ammonia or a lower alkyl amine (e.g. $CH_3CH_2NH_2$), an ether such as diethyl ether or tetrahydrofuran, and a lower alcohol. Desirably, the reaction is carried out with excess sodium (5 to 10 equivalents) in liquid ammonia containing tetrahydrofuran and t-butyl alcohol; the ratio of ammonia:tetrahydrofuran:t-butyl alcohol being 2:1:1. This results in production of an enol ether having the structure:

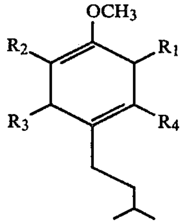

XI which is purified by chromatography. The so-formed enol ether can be hydrolyzed in the presence of an aqueous mineral acid (e.g. HCl) containing a cosolvent such as acetone or tetrahydrofuran at room temperature to produce enone IX which has valuable organoleptic properties.

Reduction of the carbonyl in compound IX with a suitable metal hydride such as diisobutylaluminum hydride or lithium aluminum hydride yields alcohol X wherein $R_5$ is hydrogen. Alcohol X is also useful in perfume or flavor compositions. Alternatively, the enone IX may be reacted with an appropriate organometallic reagent (e.g. $R_5MgX$ where $R_5$ is lower alkyl) under conditions similar to those described above for ketone V; this leads to formation of alcohol X wherein $R_5$ is lower alkyl.

Recovery and purification of the various final products of the present invention is achieved by conventional techniques including extraction, distillation, crystallization, preparative chromatographic separation and the like.

The alicyclic ketones and alcohols of this invention possess distinctive balsamic, woody, sweet, rooty, musty, earthy, leathery, citrus-like, herbaceous odors, and are useful in fine fragrances and in perfumed products such as soaps, detergents, deodorants, cosmetic preparations and the like.

One or more of the alicyclic ketones and alcohols and conventional fragrance ingredients, for example, alcohols, aldehydes, ketones, nitriles, esters and essential oils, may be admixed in varying quantities to produce desired fragrances. In this manner, perfume compositions may be prepared which are carefully balanced, harmonious blends and which include essential oils, aroma chemicals, resinoids and other extracts of natural odorous materials, each ingredient imparting a characteristic effect to the total composition. In such compositions, one or more of the alicyclic ketones or alcohols of the invention can be employed to impart unique characteristics.

Such compositions may contain up to about 80 percent by weight of at least one alicyclic ketone or alcohol of this invention. Ordinarily, at least about 0.001 percent by weight of alicyclic ketone or alcohol is required to impart significant odor characteristics. Amounts in the range of from about 1 to about 60 percent by weight are preferred. The alicyclic ketones and alcohols of this invention may be formulated into concentrates containing from about 1 to about 60 percent by weight in an appropriate solvent. Such concentrates may then be employed to fomulate such products as colognes, soaps, etc., wherein the final concentration of the compound or compounds can vary from about 0.001 to about 7 percent by weight, depending upon the final product. For example, the concentration will be about 0.001 to about 0.1 percent by weight in detergents, and about 0.01 to about 7 percent by weight in perfumes and colognes.

The alicyclic ketones and alcohols of this invention are useful as olfactory components in detergents and soaps; space odorants and deodorants; perfumes; colognes; toilet water; bath preparations such as bath oils and bath solids; hair preparations such as lacquers, brilliantines, pomades and shampoos; cosmetic preparations such as creams, deodorants, hand lotions and sunscreens; and powders such as talcs, dusting powders and face powders.

The alicyclic ketones and alcohols of this invention have also been found useful in altering the flavor component or components of flavor compositions. Thus, the compounds are effective in imparting a certain natural character to artificial flavors. They also can be employed to modify the organoleptic properties of consumables such as chewing gums, beverages, pharmaceutical preparations, fruit juices, and the like.

The specific flavoring properties of the alicyclic ketones and alcohols of this invention depend upon the type of product to which they are added. In general, they develop woody, earthy, minty, fruity, citrus-like flavor notes or combinations thereof. Therefore, they can be employed advantageously in certain citrus products such as orange oil to round off the taste and in pineapple flavors to enhance the taste and aroma.

In flavor compositions, the concentration of the alicyclic ketones and alcohols can also vary widely depending upon the organoleptic properties desired. Typically, interesting flavor effects can be obtained with concentrations from about 0.001 to about 1 percent by weight of the compound or compounds in the final flavor composition. In some situations, higher concentrations are required to produce special flavoring effects. For example, in artificial flavor compositions, one or more compounds may be incorporated in amounts such that the total is 20 percent by weight or higher.

One or more of the alicyclic ketones or alcohols of this invention may also be added to smoking tobacco or synthetic tobacco where they impart woody, amber-like, and cedarwood notes to the tobacco aroma. In tobacco compositions, the concentrations are preferably between about 1 and about 100 ppm, although in certain situations, higher levels may be usefully employed.

The following examples are set forth to illustrate preferred methods of synthesizing the compounds of this invention, and their use in flavor and fragrance compositions. Where appropriate, data including data from nuclear magnetic resonance, infrared, and mass spectra have been included to confirm that various compounds have in fact been prepared. Unless otherwise indicated, all percentages are by weight. These examples are intended only to illustrate the preferred embodiments of this invention, and are in no way meant to limit its scope.

EXAMPLE 1

Preparation of 2,6-Dimethyl-4-(3-methyl-2-butenyl)phenol

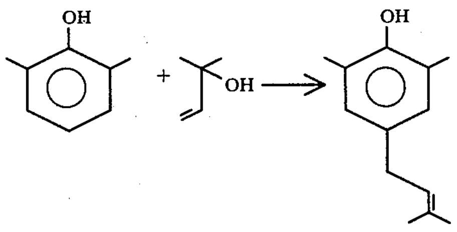

To a mixture of 2,6-dimethylphenol (122 g, 1 mol) and 85% phosphoric acid (60 mL) was added 2-methyl-3-buten-2-ol (103 g, 1.2 mol) with efficient stirring at 35°–43° C. during 1 h. After stirring for an additional 3.5 h at 25° C., the mixture was quenched into ice and extracted with hexane. The combined hexane extracts were washed successively with 1 N sodium hydroxide (100 mL), 5% sodium bicarbonate (300 mL) and brine (200 mL). The organic layer was dried, the solvent evaporated, and the residue fractionated to yield 92 g of 2,6-dimethyl-4-(3-methyl-2-butenyl)phenol bp 108°–111° C. (1 mm). NMR ($CDCl_3$) δ1.7 (6H, s), 2.2 (6H, s), 3.2 (2H, bd), 4.4 (1H, s, exchanged with $D_2O$), 5.3 (1H, m), 6.8 (2H, s). IR (film) 3500, 1225, 1150, 870 $cm^{-1}$. MS (m/e) 190 ($M^+$), 175, 160, 135, 91.

EXAMPLE 2

Preparation of 2,3,6-Trimethyl-4-(3-methyl-2-butenyl)phenol

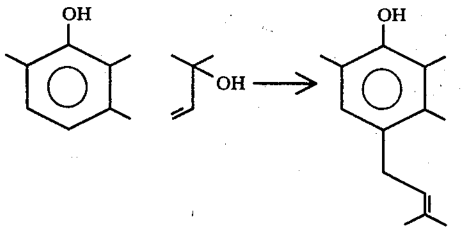

2,3,6-Trimethylphenol (68 g, 0.5 mol) and formic acid (100 mL) were combined and warmed to 50°-55° C. with vigorous agitation. To this mixture was added 2-methyl-3-buten-2-ol (47.3 g, 0.55 mol) dropwise over 0.25 h. The reaction mixture was stirred for an additional 2 h at 50° C., and then quenched into water 8300 mL). The crude product was isolated by extraction with toluene (3×100 mL) followed by washing with water (200 mL), 5% sodium bicarbonate (2×100 mL), and brine (3×100 mL). Evaporation of the solvent and distillation afforded 61 g of the phenol, bp 145°-150° c. (2 mm). NMR ($CDCl_3$) δ1.7 (6H, s), 2.2 (9H, s), 3.2 (2H, bd), 4.4 (1H, s, exchanged with $D_2O$), 5.2 (1H, m), 6.8 (1H, s). IR (film) 3700, 1460, 1200, 1090 $cm^{-1}$. MS (m/e) 204 (M+), 189, 174, 190, 136.

EXAMPLE 3

Preparation of 2,3,5,6-Tetramethyl-4-(3-methyl-2-butenyl)phenol

The phenol was prepared by the method described in Example 2 except 2,3,5,6-tetramethylphenol was used instead of the trimethylphenol. The phenol was recrystallized from hexane, mp 105°-106° C. NMR ($CDCl_3$) 2.2 (12H, s), 2.7 (6H, 2 s), 3.3 (2H, d), 4.5 (1H, s, exchanged with $D_2O$). IR ($CHCl_3$) 3590, 2700, 1440, 1200, 1090 $cm^{-1}$. MS (m/e) 218 (M+), 203, 188, 150, 135.

EXAMPLES 4-7

Hydrogenation of 2,6-Dimethyl-4-(3-methyl-2-butenyl)phenol

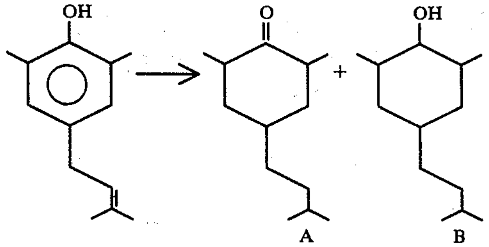

A B

The data set forth in Table I show the results obtained upon hydrogenation of 2,6-dimethyl-4-(3-methyl-2-butenyl)phenol using several different catalysts and solvents.

TABLE I

| Example | Catalyst | Solvent | Pressure (psig) | Temp. (°C.) | Result |
|---|---|---|---|---|---|
| 4 | $PtO_2$ | HOAc | 200-300 | 50° | <95% alcohol B |
| 5 | 5% Rh/C | hexane | 50-70 | 25° | 50% ketone A<br>50% alcohol B |
| 6 | 5% Pd/C | neat | 200-300 | 175° | 70% ketone A<br>30% alcohol B |
| 7 | 5% Pd/C | neat | 300 | 200° | 40% ketone A<br>60% alcohol B |

The reaction conditions of Example 4 resulted in formation of 2,6-dimethyl-4-(3-methylbutyl)cyclohexanol, bp 98°-101° C. (3 mm). GLC analysis of this alcohol shows it to be mainly (86%) one isomer. NMR ($CDCl_3$) δ0.8-1.1 (12H, m), 1.1-2.0 (13H, complex pattern), 3.5 (1H, bs). IR (film) 3450, 1160, 970, 935 $cm^{-1}$. MS (m/e) 198 (M+), 109, 71, 59, 85.

EXAMPLE 8

Preparation of 2,6-Dimethyl-4-(3-methylbutyl)cyclohexanone

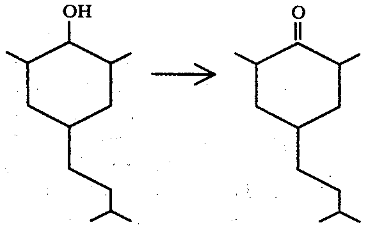

Jones reagent (150 mL) was added dropwise at room temperature to a solution of 2,6-dimethyl-4-(3-methylbutyl)cyclohexanol (100 g, 0.5 mol, produced according to Example 4) in acetone (3,000 mL). The reaction mixture was stirred for 1 h and isopropanol added to decompose excess Jones reagent. The salts were removed by filtration and the solution concentrated on a rotary evaporator. The residue was taken up in ethyl acetate and washed successively with water (400 mL), 5% sodium bicarbonate (200 mL) and brine (200 mL). The organic layer was dried, the solvent evaporated, and the residue fractionated to yield 71 g of the ketone, bp 96°-100° C. (3 mm). NMR ($CDCl_3$) δ0.8-1.1 (12H, m), 1.1-3.2 (12H, m). IR (film) 1725, 1140, 990 $cm^{-1}$. MS (m/e) 196 (M+), 69, 82, 97, 41.

EXAMPLE 9

Preparation of 1,2,6-Trimethyl-4-(3-methylbutyl)cyclohexanol

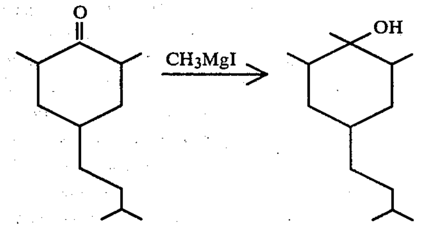

To a Grignard solution prepared from magnesium (14.5 g, 0.6 g-atom) and methyl iodide (85.2 g, 0.6 mol) in anhydrous ether (500 mL) was added 2,6-dimethyl-4-(3-methylbutyl)cyclohexanone (59 g, 0.3 mol, produced according to Example 8) over 1 h at 15°-20° C. The mixture was stirred for an additional 1 h and then quenched into saturated ammonium chloride solution. The layers were separated and the aqueous solution was extracted with ether. The combined extracts were washed with 5% sodium bicarbonate solution, brine and then dried. Solvent removal and distillation gave 40 g of the alcohol, bp 92° C. (1 mm). NMR ($CDCl_3$) δ0.8–1.1 (12H, m), 1.1–2.2 (16H, complex pattern with a singlet at 1.2). IR (film) 3550, 1025, 920, 890 $cm^{-1}$. MS (m/e) 212 (M+), 85, 43, 57, 86.

EXAMPLE 10

Preparation of 2,3,6-Trimethyl-4-(3-methylbutyl)cyclohexanol

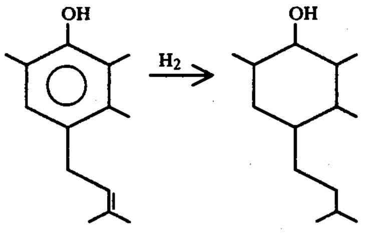

A mixture of 2,3,6-trimethyl-4-(3-methyl-2-butenyl)-phenol (30 g, 0.15 mol), platinum oxide (3 g), and acetic acid (150 mL) was hydrogenated at 50° C. and 200–300 psig until hydrogen uptake ceased. The mixture was filtered to remove the catalyst and the filtrate poured into water. The product was extracted with ethyl acetate and the extract washed successively with water, 5% sodium bicarbonate solution, and brine. The organic layer was dried, the solvent removed, and the residue fractionated to afford 17 g of the desired alcohol, bp 105°–110° C. (1 mm). NMR ($CDCl_3$) δ0.7–2.2 (27H, complex pattern), 3.6 (1H, bs). IR (film) 3700, 1500, 1020, 970 $cm^{-1}$. MS (m/e) 212 (M+), 123, 35, 69, 95.

EXAMPLE 11

Hydrogenation of 2,3,5,6-Tetramethyl-4-(3-methyl-2-butenyl)phenol

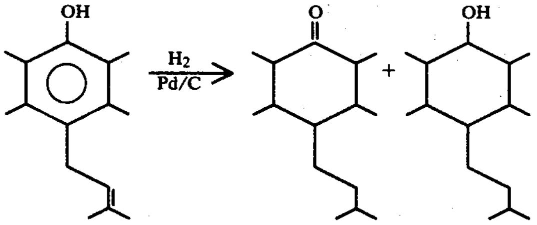

2,3,5,6-Tetramethyl-4-(3-methyl-2-butenyl)phenol (10 g, 0.046 mol, prepared according to Example 3), 5% palladium on carbon (1 g), and cyclohexane (20 mL) were mixed in an autoclave and heated to 160° C. under 250–300 psig of hydrogen. When hydrogen uptake ceased, the mixture was cooled, an additional amount of 5% palladium on carbon (1 g) added, and hydrogenation continued until no more phenol was detected. The cooled reaction mixture was filtered, the solvent evaporated, and the residue distilled to yield 7 g of material, bp 92° C. (0.5 mm). Spectral analysis (nmr, glc/ms, ir) of the distillate confirmed the presence of both ketone and alcohol in the hydrogenation product (20% and 80% respectively).

ketone: MS (m/e) 224 (M+), 137, 83, 69, 85
alcohol: MS (m/e) 208 (M+−18), 137, 69, 83, 55

EXAMPLE 12

Preparation of 2,6-Dimethyl-4-(3-methylbutyl)anisole

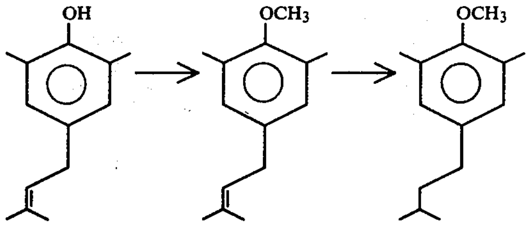

A solution of dimethyl sulfate (100 g, 0.79 mol) and 2,6-dimethyl-4-(3-methyl-2-butenyl)phenol (40 g, 0.21 mol) was added over 0.5 h at 30°–50° C. to a solution of sodium hydroxide (50 g, 1.25 mol) in water (50 mL) containing Adogen 464 (6 g). The reaction mixture was agitated overnight followed by addition of water (200 mL).

The product was isolated by extraction with toluene (2×150 mL), and the combined extracts washed with water. The solvent was evaporated and the residue distilled to afford 33.5 g of the desired ether, bp 109°–110° (3 mm). NMR ($CDCl_3$) δ1.7 (6H, s), 2.1 (6H, s), 3.2 (2H, d), 3.7 (3H, s), 5.3 (1H, m), 6.8 (2H, s). IR (film) 1225, 1150, 1050, 870 $cm^{-1}$. MS (M/e) 204 (M+), 189, 173, 91.

A solution of 2,6-dimethyl-4-(3-methyl-2-butenyl)-anisole (10 g, 0.05 mol) in isopropanol (20 mL), together with 5% palladium on carbon (0.1 g) was hydrogenated in a Parr apparatus until the theoretical amount of hydrogen had been consumed. The catalyst was removed by filtration and the solvent evaporated to give a clear residue which was fractionated to afford 7.1 g of the desired product, bp 102°–105° C. (2 mm). NMR ($CDCl_3$) δ0.9 (6H, d), 1.1–2.0 (3H, m), 2.2 (6H, s), 2.5 (2H, t), 3.7 (3H, s), 6.85 (2H, s). IR (film) 3000, 1225, 1025, 870 $cm^{-1}$. MS (m/e) 206 (M+), 149, 150, 135, 191.

EXAMPLE 13

Preparation of 2,6-Dimethyl-4-(3-methylbutyl)2-cyclohexen-1-one

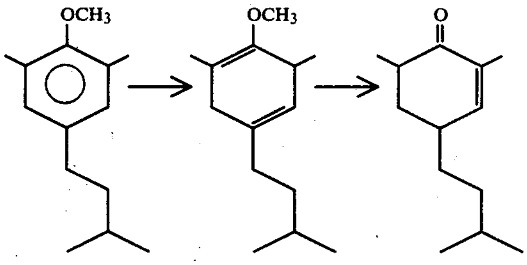

A solution of 2,6-dimethyl-4-(3-methylbutyl)anisole (8.5 g, 0.042 mol, prepared according to Example 12), in a mixture of t-butyl alcohol (180 mL) and tetrahydrofuran (180 mL) was added with efficient stirring to ammonia at −30° C. To the resulting solution was added sodium metal (15 g, 0.65 g-atom) in small portions over 1 h. The mixture was stirred for an additional 3 h at −30° C. followed by cautious addition of methanol (100 mL). The ammonia was allowed to evaporate and water (500 mL) was added. The mixture was extracted with hexane, washed with water, and dried. Solvent removal afforded 8.0 g of the enol ether. A small sample was purified by chromatography to obtain spectral data. NMR ($CDCl_3$) δ0.8–1.2 (9H, m), 1.2–3.0 (9H, complex pattern with broad singlet at 1.7), 3.6 (3H, s), 5.4 (1H, bs). IR (film) 1672, 1450 $cm^{-1}$. MS (m/e) 208 (M+), 137, 71, 43, 91.

The enol ether was added to a mixture of acetone (150 mL) and 6 N HCl (16 mL) and stirred at room temperature for 20 h. The acetone was removed on a rotary evaporator and residual liquid extracted with hexane. The combined hexane extracts were washed with 5% sodium bicarbonate and brine. The organic layer was dried, the solvent evaporated, and the crude enone purified by silica gel chromatography (hexane/ethyl acetate 90:10). The enone was a mixture of two isomers by glc (65:35). NMR ($CDCl_3$) δ0.7–1.2 (6H, complex), 1.2–2.6 (12H, complex with singlet at 1.8), 6.6 (1H, bs). IR (film) 1690, 1490, 1050 $cm^{-1}$. MS (m/e) 194 (M+), 95, 82, 96, 109.

EXAMPLE 14

Preparation of 2,6-Dimethyl-4-(3-methylbutyl)-2-cyclohexen-1-ol

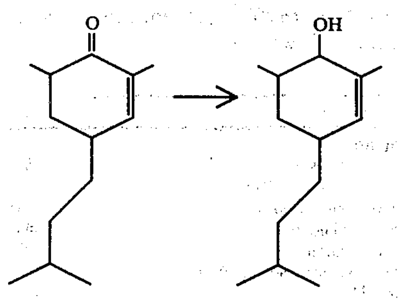

A suspension of lithium aluminum hydride (0.5 g, 0.013 mol) in anhydrous diethyl ether (100 mL) was stirred at 10° C. under nitrogen while 2,6-dimethyl-4-(3-methylbutyl)-2-cyclohexen-1-one (5.8 g, 0.03 mol) in anhydrous ether (10 mL) was added over a period of 30 minutes. The mixture was stirred at room temperature for 3 hours; then it was treated successively with water (0.5 mL), 15% NaOH solution (0.5 mL), and water (1.5 mL). The solution was filtered, dried and concentrated to give the crude alcohol. Short path distillation afforded 5.0 g of 2,6-dimethyl-4-(3-methylbutyl)-2-cyclohexen-1-ol, bp 90°–95° C. (1 mm), as a mixture of isomers by glc/ms (65.5%, 28%, and 5.5%). NMR ($CDCl_3$) δ0.9–1.6 (19H, complex), 1.8 (3H, bs), 3.6 (1H, m), 5.4 (1H, m). IR (film) 3300, 1040, 1010 $cm^{-1}$. MS (m/e) 196 (M+), 98, 82, 125, 107.

EXAMPLE 15

Preparation of 3,5-Dimethyl-4-(3-methyl-2-butenyl)phenol

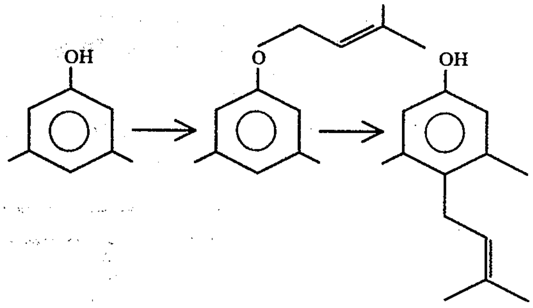

A solution of 3,5-dimethylphenol (122 g, 1 mol) in dimethylacetamide (200 mL) was added over 2 h at 30°–40° C. to a slurry of 50% sodium hydride (60 g, 1.25 mol) in dimethylacetamide (1500 mL). The reaction mixture was stirred at 50° C. for an additional 2 h, cooled to 30° C. and prenyl chloride (155 g, 1.5 mol) was added over 1 h. After stirring at 50° C. overnight, the mixture was cooled and quenched into water (4,000 mL). The product was extracted with toluene (4×300 mL), and the combined extracts washed with brine. The solvent was evaporated and the residue fractionated to give 142 g of the prenyl ether, bp 106°–110° C. (3 mm). NMR ($CDCl_3$) δ1.8 (6H, bs), 2.3 (6H, s), 4.4 (2H, d), 5.5 (1H, m), 6.5 (3H, s). IR (film) 1600, 1290, 1050 $cm^{-1}$. MS (m/e) 190 (M+), 122, 107, 69, 41.

The prenyl ether (80 g, 0.42 mol) was heated in a nitrogen-purged autoclave for 24 h at 170°–180° C. The crude material obtained by this process was distilled to afford 67.8 g of 3,5-dimethyl-4-(3-methyl-2-butenyl)-phenol, bp 115°–120° C. (0.5 mm). The phenol was recrystallized from hexane, mp 64°–65° C. NMR ($CDCl_3$) δ1.6 (3H, bs), 1.8 (3H, bs), 2.2 (6H, s), 3.2 (2H, bs), 4.9 (1H, m), 5.3 (1H, exchanged with $D_2O$), 6.5 (2H, s). IR ($CHCl_3$) 3350, 1590, 1210, 740 $cm^{-1}$. MS (m/e) 190 (M+), 175, 134, 135, 160.

EXAMPLE 16

Hydrogenation of 3,5-Dimethyl-4-(3-methyl-2-butenyl)phenol

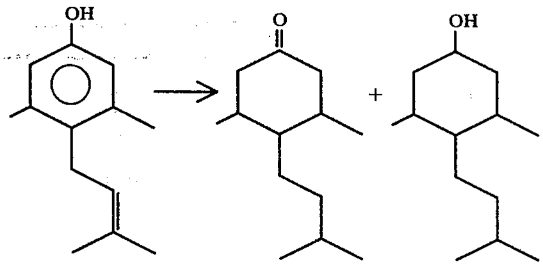

3,5-Dimethyl-4-(3-methyl-2-butenyl)phenol (25 g, 0.13 mol, prepared according to Example 15), 5% palladium on carbon (1.25 g) and sec-butyl alcohol (10 mL) were mixed in an autoclave and heated to 200° C. under 250–300 psig of hydrogen. When the hydrogen uptake ceased, the mixture was cooled, an additional amount of 5% palladium on carbon (1.25 g) added, and hydrogenation continued until no more phenol was detected.

The cooled reaction mixture was filtered, the solvent evaporated and the residue distilled to afford 19 g of material, bp 105°-113° C. (3 mm). Spectral analysis (nmr, ir, glc, ms) of the distillate confirmed the presence of both ketone and alcohol (39% and 61% respectively) in the hydrogenation product.

ketone: MS (m/e) 196 (M+), 69, 41, 55, 57 alcohol: MS (m/e) 180 (M+-18), 109, 43, 55, 57

EXAMPLE 17

A perfume base was prepared by mixing the following:

| Component | % |
|---|---|
| Isobutyl quinoline/1% in DEP | 0.1 |
| Furfural/1% in DEP | 0.1 |
| Geraniol | 0.1 |
| Methyl nonyl ketone | 0.1 |
| Cedrol | 0.2 |
| Geranyl acetate | 2.6 |
| Terpinyl acetate | 4.0 |
| Dipropylene glycol | 7.0 |
| Ionone residue | 8.2 |
| Oil Copaiba | 13.1 |
| Cedarwood acetate | 13.2 |
| Oil Guaiacwood | 16.3 |
| 2,6-Dimethyl-4-(3-methylbutyl) cyclohexanol | 35.0 |
| | 100.0 |

EXAMPLE 18

A perfume base was prepared by mixing the following:

| Component | % |
|---|---|
| Oil Copaiba | 1.0 |
| Benzyl cinnamate | 2.0 |
| Oil Guaiacwood | 2.5 |
| Cedrenyl acetate | 5.0 |
| Oil Balsam gurjon | 85.0 |
| 2,6-Dimethyl-4-(3-methylbutyl) cyclohexanone | 4.5 |
| | 100.0 |

EXAMPLE 19

A floral bouquet was prepared by mixing the following:

| Component | % |
|---|---|
| Musk ketone | 1.0 |
| Coumarin | 1.0 |
| Methyl everninate | 0.5 |
| Oakmoss absolute | 0.5 |
| Geraniol | 10.0 |
| Phenylethyl alcohol | 16.0 |
| Citronellol | 2.0 |
| Geranyl acetate | 1.0 |
| Indole 10% | 1.0 |
| Rose otto | 3.0 |
| Rose oxide 10% | 1.0 |
| Hydroxycitronellal | 14.0 |
| Pentadecanolide | 1.0 |
| Methyl dihyrojasmonate | 10.0 |
| Hexyl cinnamic alcohol | 10.0 |
| Benzyl acetate | 1.0 |
| Oil Ylang extra | 0.5 |
| Cinnamic alcohol | 0.5 |
| Phenylethyl acetate | 0.5 |
| Gamma undecalactone 10% | 0.5 |
| Cyclamen aldehyde | 0.5 |

-continued

| Component | % |
|---|---|
| Ionone alpha | 0.5 |
| Methylionone gamma | 4.0 |
| Cedroxyde | 4.0 |
| Acetyl cedrene | 8.0 |
| Oil Bergamot rect. | 3.0 |
| 2,6-Dimethyl-4-(3-methylbutyl) cyclohexanone | 5.0 |
| | 100.0 |

EXAMPLE 20

A violet fragrance composition was prepared by mixing the following:

| Component | % |
|---|---|
| Musk ambrette | 0.6 |
| Jasmin absolute | 0.3 |
| Violet leaves absolute | 0.1 |
| Heliotropin | 1.0 |
| Methylionone | 3.0 |
| Benzoin Siam | 2.0 |
| Oil Cedarwood | 20.0 |
| Oil Sandalwood | 30.0 |
| Oil Orris Root | 40.0 |
| Mixture of 3,5-dimethyl-4-(3-methylbutyl) cyclohexanone and 3,5-dimethyl-4-(3-methylbutyl) cyclohexanol (from process of Example 16) | 3.0 |
| | 100.0 |

EXAMPLE 21

A fougere type perfume composition was prepared by mixing the following:

| Component | % |
|---|---|
| Coumarin | 5.0 |
| Musk ambrette | 5.0 |
| Musk aldehyde FDO | 5.0 |
| Methylionone gamma | 4.0 |
| Isoamyl salicylate | 4.0 |
| Oil Galbanum | 0.5 |
| Delta decalactone (1% in DEP) | 0.5 |
| Santol FDO | 4.0 |
| Oil Patchouly | 6.0 |
| Oakmoss absolute incolore | 4.0 |
| Oil Neroli - Base | 7.0 |
| Oil Geranium Maroc | 10.0 |
| Phenylethyl alcohol | 3.0 |
| Oil Bergamot | 7.0 |
| Linalool synthetic | 6.0 |
| Oil Lavender 50-52% | 10.0 |
| Eugenol extra | 2.0 |
| Isoeugenol | 1.0 |
| Benzyl benzoate | 4.0 |
| 2,6-Dimethyl-4-(3-methylbutyl) cyclohexanol | 12.0 |
| | 100.0 |

EXAMPLE 22

An oil vetiver substitute was prepared by mixing the following:

| Component | % |
|---|---|
| Oil Patchouly | 1.0 |
| Geraniol ex Palmarosa | 1.0 |
| Ionone residue | 3.0 |
| Oil Copaiba | 12.0 |

-continued

| Component | % |
|---|---|
| Cedryl acetate | 13.0 |
| Oil Guaiacwood | 16.0 |
| Oil Cedarwood | 15.0 |
| Terpineol | 5.0 |
| Oil Bois de Rose | 9.0 |
| Mixture of 2,6-dimethyl-4-(3-methylbutyl) cyclohexanone and 2,6-dimethyl-4-(3-methylbutyl) cyclohexanol (from process of Example 6) | 25.0 |
| | 100.0 |

EXAMPLE 23

A jasmin fragrance was prepared by mixing the following:

| Component | % |
|---|---|
| Gamma undecalactone | 0.5 |
| p-Cresyl phenylacetate | 0.5 |
| Ethyl cinnamate | 0.9 |
| Oil Ylang extra | 7.0 |
| Geranyl acetate | 6.0 |
| Amylcinnamic aldehyde | 5.0 |
| Linalool synthetic | 10.0 |
| Benzyl acetate | 20.0 |
| Phenylethyl alcohol | 20.0 |
| Hydroxycitronellal | 30.0 |
| 2,6-Dimethyl-4-(3-methylbutyl)-2-cyclohexen-1-one | 0.1 |
| | 100.0 |

EXAMPLE 24

Modified Orange Flavor

| Component | A (%) | B (%) | C (%) |
|---|---|---|---|
| Oil Orange | 53.9 | 53.9 | 53.9 |
| Oil Lemon | 10.0 | 10.0 | 10.0 |
| 1,1-Diethoxyethane | 1.5 | 1.5 | 1.5 |
| Ethyl butyrate | 3.2 | 3.2 | 3.2 |
| Allyl hexanoate | 0.6 | 0.6 | 0.6 |
| Linalool | 2.6 | 2.6 | 2.6 |
| Undecanol | 2.4 | 2.4 | 2.4 |
| Benzyl alcohol | 25.8 | 24.8 | 24.8 |
| 2,6-Dimethyl-4-(3-methylbutyl) cyclohexanol | — | 1.0 | — |
| 2,6-Dimethyl-4-(3-methylbutyl) cyclohexanone | — | — | 1.0 |
| | 100.0 | 100.0 | 100.0 |

The above formulations were added at a level of 20 ppm to a beverage medium consisting of sugar, acid, and water. In tests, compositions B and C were both preferred over the control flavor. The contribution of both 2,6-dimethyl-4-(3-methylbutyl)cyclohexanol and 2,6-dimethyl-4-(3-methylbutyl)cyclohexanone to the overall flavor character was attributed to the development of a "cooked" citrus quality in the final composition.

EXAMPLE 25

Pineapple Flavor Composition

| Component | A (%) | B (%) | C (%) |
|---|---|---|---|
| Allyl cyclohexane propionate | 1.4 | 1.4 | 1.4 |
| Geranyl propionate | 0.5 | 0.5 | 0.5 |
| Allyl caproate | 13.0 | 13.0 | 13.0 |
| Ethyl isovalarate | 1.0 | 1.0 | 1.0 |
| Ethyl butyrate | 1.0 | 1.0 | 1.0 |
| Vanillin | 0.5 | 0.5 | 0.5 |
| Oil Orange | 1.0 | 1.0 | 1.0 |
| Maltol | 2.0 | 2.0 | 2.0 |
| Ethyl alcohol (95%) | 48.5 | 47.5 | 47.5 |
| Propylene glycol | 31.1 | 31.1 | 31.1 |
| 2,6-Dimethyl-4-(3-methylbutyl) cyclohexanone | — | 1.0 | — |
| 2,6-Dimethyl-4-(3-methylbutyl) cyclohexanol | — | — | 1.0 |
| | 100.0 | 100.0 | 100.0 |

The above pineapple flavor compositions were evaluated by a panel at a level of 30 ppm in a standard beverage medium consisting of sugar, acid, and water. Compositions B and C were both preferred over the control. There was a marked improvement in the overall flavor character resulting in a more natural flavor.

EXAMPLE 26

A chypre type perfume composition was prepared by mixing the following:

| Component | % |
|---|---|
| Oil Angelica Root | 0.5 |
| Castoreum absolute | 0.5 |
| Oil Rose | 1.0 |
| Civet absolute | 1.0 |
| Oakmoss absolute | 1.0 |
| Musk ambrette | 2.0 |
| Labdanum resinoid | 3.0 |
| Oil Ylang extra | 5.0 |
| Benzyl acetate | 6.0 |
| Oil Sandalwood | 7.0 |
| Vanillin | 6.0 |
| Benzyl alcohol | 9.0 |
| Jasmin extract | 12.0 |
| Coumarin | 12.0 |
| Phenylethyl alcohol | 12.0 |
| Oil Bergamot | 20.0 |
| 2,6-Dimethyl-4-(3-methylbutyl)-2-cyclohexen-1-ol | 2.0 |
| | 100.0 |

EXAMPLE 27

A 1% ethanol solution of 2,6-dimethyl-4-(3-methylbutyl)cyclohexanone was sprayed on a typical smoking tobacco in an amount sufficient to provide a tobacco composition containing 20 ppm of the flavor additive on a dry basis. Cigarettes were prepared from the treated tobacco and evaluated by a panel. In the panel evaluation against control cigarettes the taste of flavored cigarettes was described as light and woody. The 2,6-dimethyl-4-(3-methylbutyl)cyclohexanone increased the body and fullness of the tobacco flavor and enhanced the overall flavor character in the smoke.

What is claimed is:

1. A fragrance composition which comprises at least one compound having the structure:

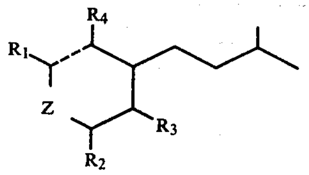

wherein the dashed line represents either a carbon-carbon double bond or a carbon-carbon single bond; wherein Z is either

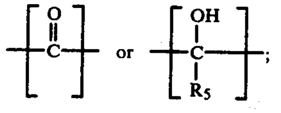

and wherein each of $R_1$, $R_2$, $R_3$, $R_4$ and $R_5$ is hydrogen or $C_1$ to $C_4$ alkyl, in an amount effective to impart fragrance thereto and conventional fragrance ingredients.

2. A fragrance composition which comprises at least one compound having the structure:

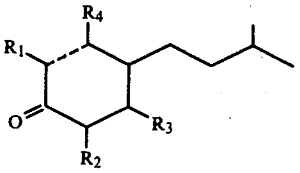

wherein the dashed line represents either a carbon-carbon double bond or a carbon-carbon single bond and wherein each of $R_1$, $R_2$, $R_3$ and $R_4$ is hydrogen or $C_1$ to $C_4$ alkyl, in an amount effective to impart fragrance thereto and conventional fragrance ingredients.

3. A fragrance composition which comprises at least one compound having the structure:

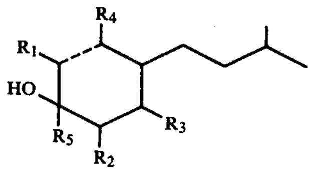

wherein the dashed line represents either a carbon-carbon double bond or a carbon-carbon single bond; and wherein each of $R_1$, $R_2$, $R_3$, $R_4$ and $R_5$ is hydrogen or $C_1$ to $C_4$ alkyl, in an amount effective to impart fragrance thereto and conventional fragrance ingredients.

4. The fragrance composition of claim 2 wherein the compound has the structure:

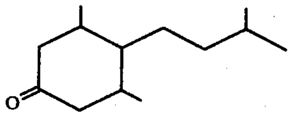

5. The fragrance composition of claim 2 wherein the compound has the structure:

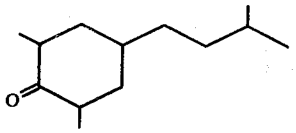

6. The fragrance composition of claim 2 wherein the compound has the structure:

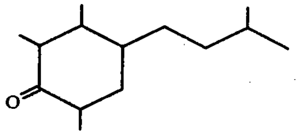

7. The fragrance composition of claim 2 wherein the compound has the structure:

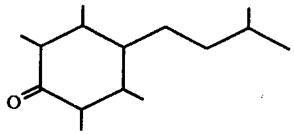

8. The fragrance composition of claim 2 wherein the compound has the structure:

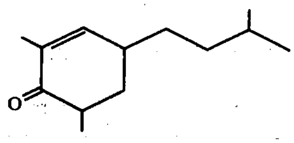

9. The fragrance composition of claim 3 wherein the compound has the structure:

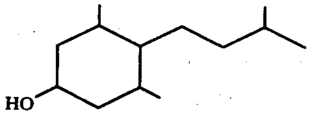

10. The fragrance composition of claim 3 wherein the compound has the structure:

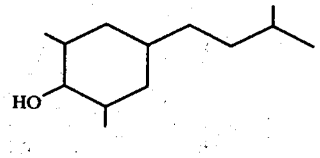

11. The fragrance composition of claim 3 wherein the compound has the structure:

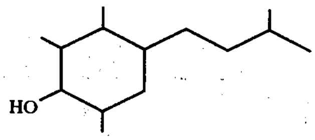

12. The fragrance composition of claim 3 wherein the compound has the structure:
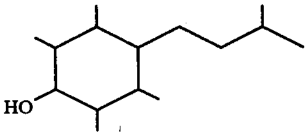
13. The fragrance composition of claim 3 wherein the compound has the structure:
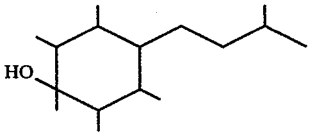
14. The fragrance composition of claim 3 wherein the compound has the structure:
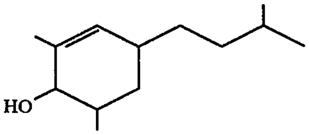
* * * * *

UNITED STATES PATENT AND TRADEMARK OFFICE

CERTIFICATE OF CORRECTION

PATENT NO. : 4,326,997

DATED : April 27, 1982

INVENTOR(S) : Brian J. Willis et al

It is certified that error appears in the above-identified patent and that said Letters Patent are hereby corrected as shown below:

Column 5, line 58, "dichloromate" should read
-- dichromate --

Column 9, line 21, "8300" should read -- (300 --

Column 9, under Table I, under the heading "Result",
" <95% alcohol B" should read
-->95% alcohol B --

Signed and Sealed this

*Twenty-second* Day of *March 1983*

[SEAL]

*Attest:*

GERALD J. MOSSINGHOFF

*Attesting Officer* *Commissioner of Patents and Trademarks*